(12) United States Patent
Vvedensky et al.

(10) Patent No.: US 8,157,800 B2
(45) Date of Patent: Apr. 17, 2012

(54) COMPUTER-AIDED SYSTEM FOR LIMB LENGTHENING

(76) Inventors: Pyotr S. Vvedensky, Nizhny Novgorod (RU); Konstantin E. Mikheev, Sarov N.-Novgorod (RU)

( * ) Notice: Subject to any disclaimer, the term of this patent is extended or adjusted under 35 U.S.C. 154(b) by 756 days.

(21) Appl. No.: 12/053,550

(22) Filed: Mar. 21, 2008

(65) Prior Publication Data

US 2008/0234554 A1    Sep. 25, 2008

(51) Int. Cl.
*A61B 17/00* (2006.01)
(52) U.S. Cl. .......................................... 606/57
(58) Field of Classification Search ............... 606/53–59, 606/86 R, 258, 63, 320
See application file for complete search history.

(56) References Cited

U.S. PATENT DOCUMENTS

| | | |
|---|---|---|
| 3,977,397 A | 8/1976 | Kalnberz et al. |
| 4,615,338 A | 10/1986 | Ilizarov et al. |
| 5,108,394 A | 4/1992 | Kurokawa et al. |
| 5,180,380 A | 1/1993 | Pursley et al. |
| 5,197,488 A * | 3/1993 | Kovacevic .................. 600/595 |
| 5,437,668 A | 8/1995 | Aronson et al. |
| 6,017,341 A * | 1/2000 | Windhagen et al. ............ 606/56 |

FOREIGN PATENT DOCUMENTS

RU    2264796 C2    4/2005

OTHER PUBLICATIONS

Wolfson N., et al., Forces and Stiffness Changes During Ilizarov Leg Lengthening, Clin Orthop Relat Res. Jan. 1990;(250):58-60.

* cited by examiner

*Primary Examiner* — Thomas J Sweet
*Assistant Examiner* — Summer Kostelnik
(74) *Attorney, Agent, or Firm* — Michelle P. Nguyen; John T. Lucas

(57) ABSTRACT

An apparatus for lengthening of extremities includes at least two supporting rings, a plurality of spikes mounted in each of the at least two supporting rings by spike-fixating elements, the at least two supporting rings connected with one another by threaded rods, which are displaced into rectilinear movement by automated drives connected with a portable block for power supply and control. Each automated drive includes a screw pair composed of a threaded rod and a threaded insert mounted via two bearings that are spaced from one another, and movable through a reducer with a stepper motor. The portable block is provided with elements for controlling a speed and a direction of movement of each of the automated drives, and a unit is provided for calculation and indication of displacement supplied by each of the automated drives.

2 Claims, 2 Drawing Sheets

COMPUTER-AIDED SYSTEM FOR LIMB LENGTHENING

CROSS-REFERENCE TO A RELATED APPLICATION

The invention described and claimed hereinbelow is a continuation-in-part of Russia Patent Application No. 2007110208 filed on Mar. 23, 2007. The Russian Patent Application, whose subject matter is incorporated herein by reference, provides the basis for a claim of priority of invention under 35 U.S.C. 119(a)-(d).

BACKGROUND OF THE INVENTION

The present invention generally relates to medicine, in particular to orthopedic medicine and traumatology, and more specifically to a system provided for lengthening of limbs by generating a dosed, non-traumatic distraction osteogenesis, with the pace of correction depending on a magnitude of distraction forces.

The amount of distraction force applied, the distraction rate, soft tissue tension, microcirculation conditions, and osteogenesis activity are all important factors in limb lengthening procedures. A critical factor to osteogenesis activity is knowledge of the force values of distraction, which allows one to timely diagnose conditions, such as, incomplete corticotomy, premature consolidation, and osteogenesis failure.

Another critical factor to osteogenesis activity is the distraction frequency. It has been shown that an increase in the distraction rhythm, e.g. (1 mm in 4-6-8 increments), ensures more favorable conditions for the formation of distraction regenerate. In addition, lengthening in an automatic microdistraction mode, e.g. (1 mm in 60 to 1840 increments), possesses a number of essential advantages. First, less tension developed in soft tissue provides more adequate microcirculation and enhanced metabolic processes in the area of bone regenerate, resulting in more active bone formation. Second, in the neuromuscular system, nerve and vessel trunks are less damaged, reducing the number of contractures in adjacent joints along with other complications. Under these conditions, the limb lengthening process more closely resembles natural physiological growth.

A challenging problem today involves measuring the tension status of the "device-patient" system during functional weight-bearing trials, which makes it possible to determine the stiffness of regenerate being formed at any period of time. What is needed is a system that can determine the stiffness of regenerate and select the optimized rhythm of lengthening. The present invention discloses an apparatus that determines bone regenerate stiffness in a corticotomy zone using external elements and that automatically adjusts the rate of lengthening to correspond to the most favorable rhythm of the patient.

SUMMARY OF THE INVENTION

Accordingly, it is an object of the present invention to provide a system with the ability to quantitatively determine the tension dynamics of the "device-patient" biomechanical system in the process of distraction osteogenesis and optimization of biomechanical modes in limb lengthening on the basis of obtained findings.

Also, another object of the present invention is to provide a system for performing a high-precision distraction osteogenesis in a mode that is safe and optimal for a patient, depending on the parameters of distraction forces.

In keeping with these objects and with others which will become apparent hereinafter, one feature of the present invention resides in a system for lengthening of limbs, comprising: at least two supporting rings; a plurality of spikes mounted in each of the at least two supporting rings by spike-fixating means; the at least two supporting rings connected with one another by threaded rods which are displaced into rectilinear movement by automated drives connected with a portable block for power supply and control; each of the automated drives including a screw pair composed of one of the threaded rods and a threaded insert mounted via two bearings and movable through reducing means with a stepper motor; the portable block being provided with elements for controlling a speed and a direction of movement of each of the automated drives; and means for calculation and indication of displacement provided by each of the automated drives.

Another feature of the present invention resides in that the inventive system has a plurality of resistors mounted on a housing of each of the automated drives over a circumference at equal distances from one another and connected through an amplification circuit and an analog-digital converter to a personal computer.

A further feature of the present invention resides in that the portable block includes an analog-digital converter and a microprocessor for constantly controlling distraction forces and adjusting an operation of autodistractors, providing correction and determination of a value of distraction forces in a predetermined safe and optimal range.

The novel features which are considered as characteristic for the present invention are set forth, in particular, in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
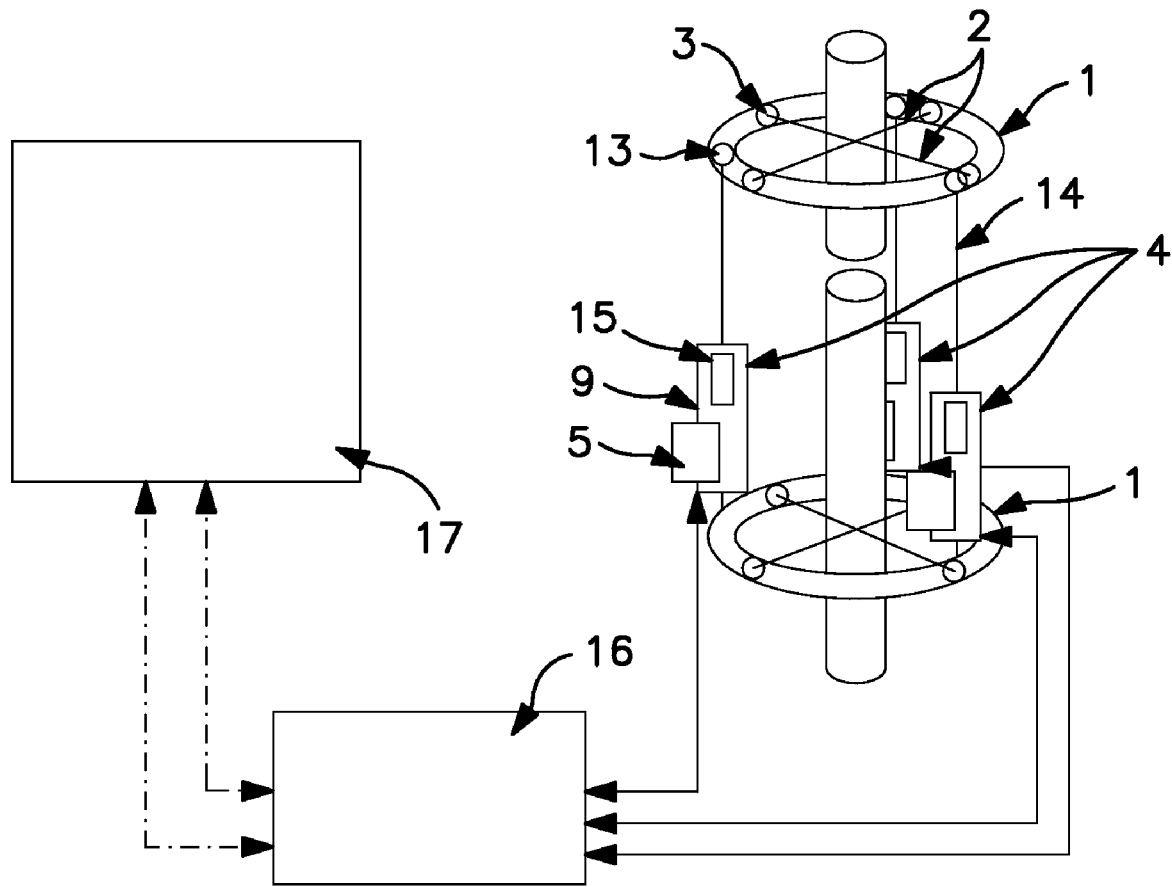
FIG. 1 is a view schematically showing a system for lengthening of limbs in accordance with the present invention.
Figure 2:
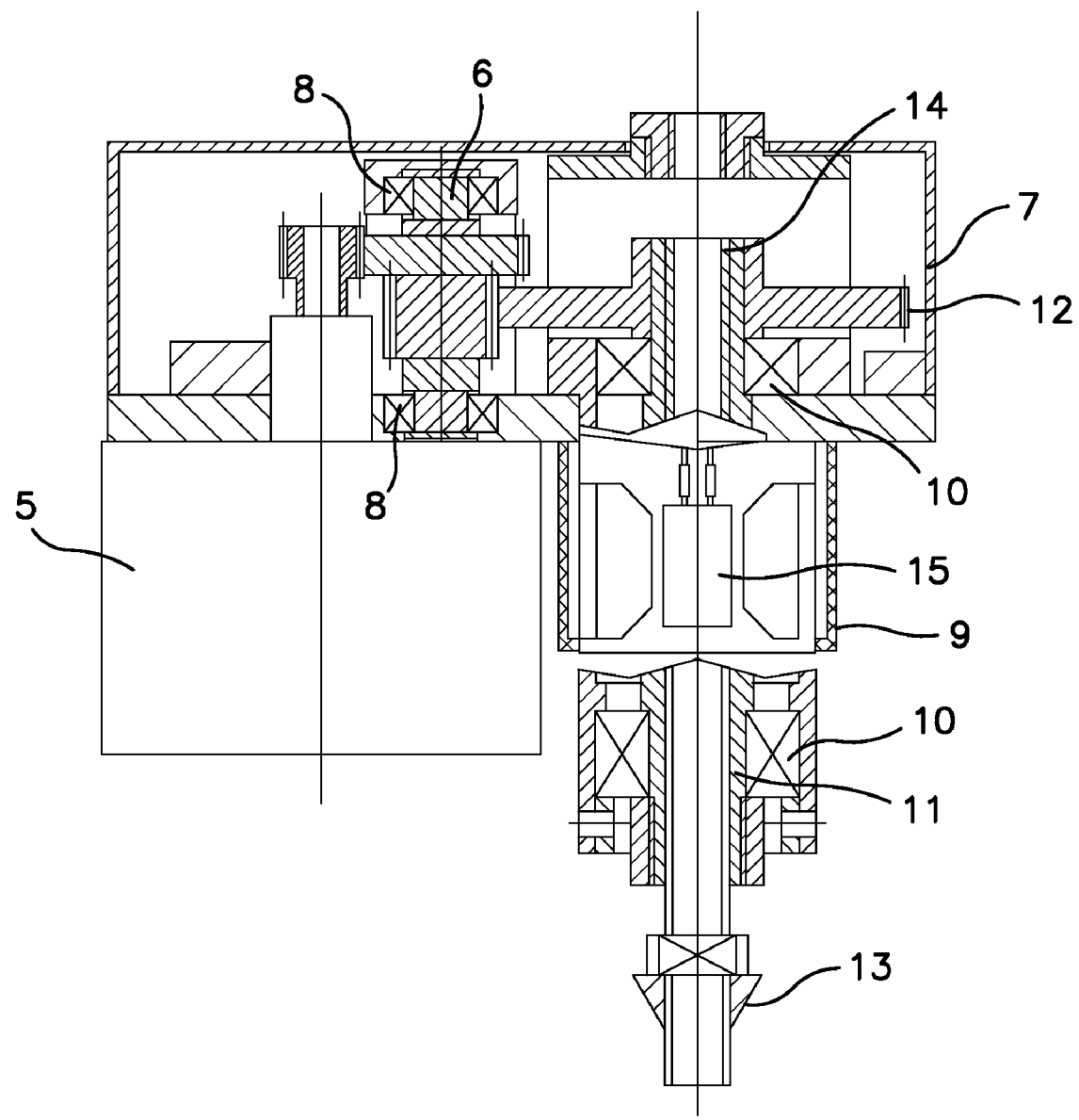
FIG. 2 is a view showing a cross-section of an automated drive of the system for lengthening of limbs.

An apparatus in accordance with the present invention has two supporting rings 1 with spikes 2 that are mounted in the rings 1 by spike-fixating elements 3, which can be of any known construction. The rings 1 are connected with one another by automated drives 4. Each drive includes a stepper motor 5, which moves an intermediate axle 6 mounted in a casing 7 via two bushings 8.

A threaded insert 11 is mounted in a housing 9 of the drive by two spaced bearings 10, and a toothed wheel 12 is arranged on the threaded insert 11. A threaded rod 14 is connected to the ring 1 by a hinge connection 13. Four resistors 15, formed as tenzoresistors of the type K5 F100 A or a similar type, are attached on the housing 9 of the drive at equal distances from one another along a circumference. Their output wires together with the supply wires of the stepper motors 5 are connected with a portable block 16 for control and power supply. The portable block 16 has batteries, a liquid-crystal indicator, a keyboard for programming of modes, and a USB port for connection to a personal computer 17, for processing the data supplied by the resistors 15.

The system for limb lengthening in accordance with the present invention operates in the following manner:

An operation is performed on a shin, and then under intravenous anesthesia, four pairs of the intersecting spikes 2 are introduced through a bone. They are tightened and fixed in the supporting rings 1 of the apparatus. The rings 1 are connected by threaded or telescopic rods 14 with one another. A corticotomy of the tibia is performed in an upper third portion and of the fibula in a lower third portion. After a latent period (5-14) days, the automated drives 4 are mounted and connected via cables to the portable block 16 for control and power supply.

When each automated drive 4 is turned on, a rotary movement is transmitted from a shaft of the stepper motor 5 via the toothed transmission of wheel 12 to the intermediate axle 6, and then to the threaded insert 11, via the screw pair of the threaded rod 14 and the threaded insert 11, which converts into rectilinear movement of the threaded rod 14.

The mounting of the threaded rod 14 to the supporting ring 1 through the hinged connection 13 prevents wedging of the screw pair due to mounting of the pair of bearings 10 spaced from one another. This results in the screw pair being resistant to wedging during tilting.

Adjustment of the length of the threaded rod is performed in a "running" mode, in which the movement of the rod is performed with a speed of 1 mm per 30 seconds. A control for maintaining correspondence of the length is performed visually, based on a movement sensor, and also indirectly via indications of a sensor in regard to the magnitude of the compression/distraction forces.

A desired speed of distraction for each rod is set by buttons on the front panel of the control and power supply block 16. A doctor can obtain information about the set speed of movement of each rod and the amount of displacement that has occurred by viewing the liquid crystal display located on the front panel of the control and power supply block 16 at any time. The force values, which are determined by the resistors 15, are transmitted through the USB port into the computer for their further processing. When the lengthening process ends, the automated drives 4 can be easily replaced with the threaded or telescopic rods 14.

Each stepper motor 5 provides independent control and tuning of the speed and direction of displacement performed by each automated drive. The system of monitoring of the distraction forces allows one to determine the value of both axial and tangential forces generated in the system "apparatus-limb". The system also allows one to exclude tangential loads on the plunger of the stepper motor.

The use of the stepper motor 5 provides simple and natural control of displacement of each automated drive in accordance with a number of carried out steps, the transmission ratio of the reduction mechanism, and the thread pitch of the screw pair "insert-rod", while the system of monitoring the magnitude of compression and distraction forces allows permanent and uninterrupted control of the process of lengthening of a limb.

It will be understood that each of the elements described above, or two or more together, may also find a useful application in other types of constructions differing from the type described above.

While the invention has been illustrated and described as embodied in an apparatus for lengthening of extremities, it is not intended to be limited to the details shown, since various modifications and structural changes may be made without departing in any way from the spirit of the present invention.

The invention claimed is:

1. A system for lengthening of limbs, comprising:
   at least two supporting rings;
   a plurality of spikes mounted in each of said at least two supporting rings by spike-fixating means;
   said at least two supporting rings connected with one another by threaded rods which are displaced into rectilinear movement by automated drives connected with a portable block for power supply and control;
   each of said automated drives including a screw pair composed of one of said threaded rods and a threaded insert mounted via two bearings and movable through reducing means with a stepper motor;
   said portable block being provided with elements for controlling a speed and a direction of movement of each of said automated drives;
   means for calculation and indication of displacement provided by each of said automated drives; and
   a plurality of resistors for sensing a distraction or compression force, said resistors mounted on a housing of each of said automated drives over a circumference at equal distances from one another and connected through an amplification circuit and an analog-digital converter to a personal computer.

2. An apparatus as defined in claim 1, wherein said portable block includes an analog-digital converter and a microprocessor for constantly controlling distraction forces and adjusting an operation of autodistractors, providing correction and determination of a value of distraction forces in a predetermined safe and optimal range.

\* \* \* \* \*